United States Patent
Furnish et al.

(10) Patent No.: US 9,345,531 B2
(45) Date of Patent: May 24, 2016

(54) RADIO-FREQUENCY TREATMENT OF SKIN TISSUE WITH SHOCK-FREE HANDPIECE

(75) Inventors: Simon Furnish, New York City, NY (US); Jonathan Achenbach, New York City, NY (US)

(73) Assignee: Cynosure, Inc., Westford, MA (US)

( * ) Notice: Subject to any disclaimer, the term of this patent is extended or adjusted under 35 U.S.C. 154(b) by 798 days.

(21) Appl. No.: 12/455,661

(22) Filed: Jun. 5, 2009

(65) Prior Publication Data
US 2010/0312233 A1  Dec. 9, 2010

(51) Int. Cl.
*A61F 2/00* (2006.01)
*A61B 18/14* (2006.01)
*A61B 18/00* (2006.01)

(52) U.S. Cl.
CPC ............. *A61B 18/14* (2013.01); *A61B 18/1402* (2013.01); *A61B 2018/00452* (2013.01); *A61B 2018/00642* (2013.01); *A61B 2018/1475* (2013.01)

(58) Field of Classification Search
USPC ........................................................ 607/101
See application file for complete search history.

(56) References Cited

U.S. PATENT DOCUMENTS

| | | | | |
|---|---|---|---|---|
| 5,997,533 | A * | 12/1999 | Kuhns ............................. | 606/41 |
| 6,749,624 | B2 * | 6/2004 | Knowlton ...................... | 607/104 |
| 7,422,586 | B2 * | 9/2008 | Morris et al. .................. | 606/41 |
| 7,473,251 | B2 * | 1/2009 | Knowlton et al. ............. | 606/41 |
| 8,321,031 | B1 * | 11/2012 | Ellman et al. ................. | 607/101 |
| 2007/0083247 | A1 * | 4/2007 | Wyeth et al. ................... | 607/99 |
| 2007/0088413 | A1 * | 4/2007 | Weber et al. .................. | 607/99 |
| 2007/0106349 | A1 * | 5/2007 | Karni et al. .................... | 607/101 |
| 2008/0183251 | A1 * | 7/2008 | Azar et al. ..................... | 607/101 |
| 2009/0112205 | A1 * | 4/2009 | McGill et al. .................. | 606/41 |

FOREIGN PATENT DOCUMENTS

| CN | 1697631 A | 11/2005 |
|---|---|---|
| WO | WO2004090939 A2 | 10/2004 |

OTHER PUBLICATIONS

Chinese-language Office Action (with English-language translation provided) dated Jul. 12, 2012, issued by China's State Intellectual Property Office in Chinese Application No. 201010201340.2, 4 pages.

* cited by examiner

*Primary Examiner* — Joseph Stoklosa
*Assistant Examiner* — Adam Avigan
(74) *Attorney, Agent, or Firm* — Ganz Pollard, LLC

(57) ABSTRACT

RF energy for skin conditioning with a non-ablative electrode is applied with a handpiece incorporating means to prevent electrical shock to the patient when the energized electrode surface makes or breaks contact with the skin. In a preferred embodiment, switch means are incorporated in the handpiece and configured such that the active electrode surface is not energized until it is in actual contact with the patient's skin, and remains energized only while the active electrode surface remains in contact with the patient's skin, so that no voltage is present on the electrode, when an air gap whose dielectric breakdown can cause an electrical shock to the patient arises, immediately before or immediately after skin contact during a skin conditioning procedure. In another preferred embodiment, the electrode to skin impedance change as the electrode touches the skin is used to activate a switch that transfers RF to the electrode.

11 Claims, 7 Drawing Sheets

RADIO-FREQUENCY TREATMENT OF SKIN TISSUE WITH SHOCK-FREE HANDPIECE

This invention relates to apparatus and a procedure for treating skin tissue using non-ablative radio-frequency energy. It also relates to novel handpieces using monopolar or bipolar electrodes for use in such procedures.

BACKGROUND OF THE INVENTION

A commonly-assigned copending application Ser. No. 11/709,672, filed Feb. 23, 2007, the contents of which are herein incorporated by reference, describes an electrode configuration and procedure for use for topical application to the tissue surface or skin of a patient for the non-ablative treatment of periorbital rhytides and midface laxity or in general removal of wrinkles or other cosmetic skin tightening procedures to improve the appearance of skin tissue.

In this radio-frequency (RF) non-ablative tissue surface treatment, it is desirable to raise the tissue temperature to about 41-65° C. to affect underlying skin collagen to tighten the surface tissue, being careful to avoid overheating the skin tissue possibly causing burns and residual scarring. To achieve this result, this prior application describes the use of specially configured electrodes to provide a reasonably uniform electric field distribution at the skin surface, pre-applying to the skin a thermal gel, a known thermally and electrically-conductive material, to help cool the surface, using low RF power, relying on the natural cooling provided by a highly conductive electrode material, and continuously manually moving the activated electrode while in contact with the skin.

A later-filed commonly-assigned copending application Ser. No. 12/012,447, filed Feb. 4, 2008, the contents of which are herein incorporated by reference, describes further RF handpieces for RF skin tightening incorporating skin temperature sensors and/or movable electrodes and/or dual electrode arrangements which can be used to spread the skin heating and to sense skin temperature to avoid overheating the skin tissue.

In the execution of such skin tightening procedures, typically the physician or other practitioner employs a foot switch to energize the handpiece which simultaneously energizes the active electrode surface of the supported electrode. An electrical shock may be felt by the patient as the energized electrode surface makes or breaks contact with the skin, as the voltage potential applied to the electrode by the RF generator is usually great enough to cause dielectric breakdown of the small air gap created when the active electrode surface is close to but not in actual physical contact with the patient's skin. This shock can cause significant discomfort to the patient.

SUMMARY OF THE INVENTION

An object of the present invention is to employ RF energy for skin conditioning with non-ablative electrodes in a handpiece incorporating means to prevent electrical shock to the patient when the energized electrode surface makes or breaks contact with the skin.

A further object of the invention is an indicator to indicate to the physician when skin contact is made or broken.

In a first group of preferred embodiments in accordance with the invention, switch means are incorporated in the handpiece and configured such that the active electrode surface is not energized until it is in actual contact with the patient's skin, and remains energized only while the active electrode surface remains in contact with the patient's skin, so that no voltage is present on the electrode, when an air gap whose dielectric breakdown can cause an electrical shock to the patient arises, immediately before or immediately after skin contact during the skin tightening procedure. "Switch means" as used in this specification and claims is defined to mean a device capable of selective electrical engagement and disengagement of electrical contacts or members.

In this first group of preferred embodiments, the electrode or its shank is movable within the handpiece but is initially physically, and thus electrically, separated from the cable or an electrical extension of the cable supplying the RF energy when the opposite end of the cable plugged into an output connector of the RF generator is energized. The structure is configured such that when the electrode is brought into contact with the skin, the pressure exerted by the physician on the handpiece moves the electrode, axially or radially, so that it or its shank electrically engages the cable or its extension so that the active electrode surface then becomes energized. Similarly, as the physician withdraws the handpiece from the patient, the first action before the electrode actually separates from the skin will be for the switch connection to be broken deenergizing the electrode immediately before the electrode-skin contact is broken.

In a second group of preferred embodiments in accordance with the invention, skin-sensing means associated with the electrode is connected to a relay in the handpiece or to the RF generator such that power is not supplied to the electrode until the sensing means indicates that the electrode has come into actual contact with the skin.

In this second group of embodiments, the sensing can be implemented with a capacitance sensor connected to the electrode, as the capacitance of the electrode to the patient's body reduces as the skin is approached and reaches a minimum on contact. Alternatively, the impedance of the RF circuit, or the output impedance at the electrode-skin interface, can be measured at the RF generator and the generator output to which the handpiece is connected energized only when the output impedance drops below a certain impedance level typically of approximately 100-200 ohms. In monopolar operation, the electrode forms one pole of the output and a neutral plate connected to the patient forms the other pole, the impedance, e.g., capacitance, measurement taking place between the poles. In bipolar operation, the two poles are formed by dual electrodes in the handpiece.

The various schemes described in the incorporated application disclosures can also be used with the handpiece of the present invention, specifically, the specially configured electrodes providing a reasonably uniform electric field distribution at the skin surface, pre-applying to the skin a gel, using RF power, relying on the natural cooling provided by a highly conductive electrode material, continuously manually moving the activated electrode while in contact with the skin, incorporating skin temperature sensors to shut down the power when the skin temperature rises too high, and means for maintaining the skin-touching active part of the electrode in continuous motion.

RF non-ablative skin tightening is preferred as it is believed that the RF technology produces an electric current that generates heat through resistance in the dermis and subcutaneous skin tissue. The thermal effect depends on the conductivity features of the treated tissue. Collagen fibrils, when heated, will denature and contract, which is believed to lead to the observed tissue tightening. Non-ablative RF treatment has a lower risk of complications, shorter recovery time and less disruption of regular activities than other skin tightening procedures.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

DETAILED DESCRIPTION OF PREFERRED EMBODIMENTS

Figure 1:
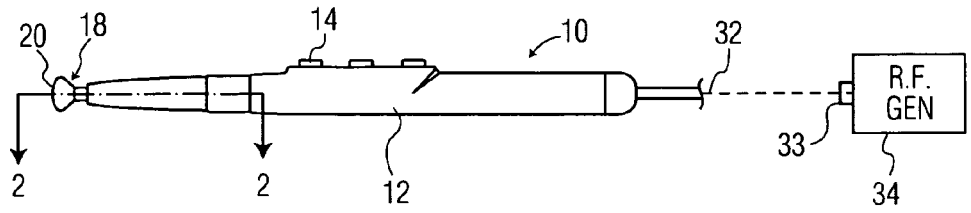
FIG. 1 is a schematic view of one form of a shock-free handpiece with a dome electrode according to the invention, shown schematically connected to an RF generator of a known type.
Figure 2:
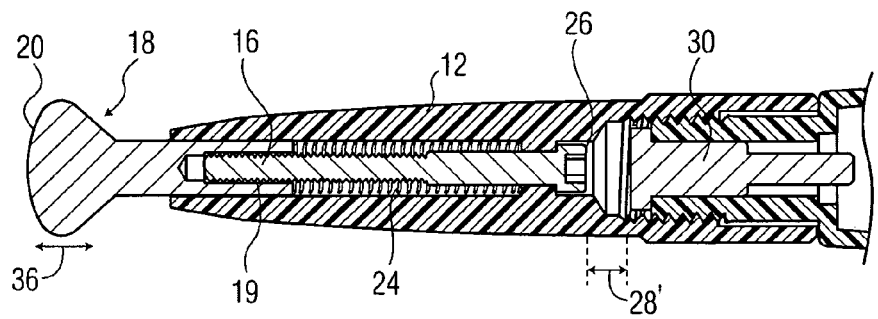
FIG. 2 is cross-sectional view along lines 2-2 of the handpiece of FIG. 1 showing the electrode in its RF-disconnected position.

In the present application, FIG. 1 is a schematic view of one form of RF applying device 10 in accordance with the invention. It comprises a handle or handpiece 12 with operating buttons 14 and with a front end adapted to receive and hold for axial movement the electrically-conductive shank end 16 of an electrically-conductive electrode 18 whose active electrode surface 20 is dome-shaped as shown. The handpiece 12 is electrically-insulating. The electrode 18 is screwed 19 onto the elongated electrically-conductive shank 16, and both move together as a unit axially within the center bore of the handle 12. Axially in FIGS. 1 and 2 is the longitudinal horizontal axis of the assembly. The electrode is biased outwardly in a first position as shown in the figure by an internal compression spring 24. The proximal end 26 of the shank, that contains a small hollow, is spaced by a contact gap 28 from a fixed electrically-conductive contact 30 mounted in a rear part of the handle, and forming at the rear a connector which internally via a circuit board connected to the operating buttons 14 (not shown) is connected at the right end for receiving an RF cable 32. FIG. 1 shows the handpiece 12 connected by the cable 32 to an output connector 33 on the chassis of a conventional RF electrosurgical generator 34, for example, of a type manufactured by Ellman International, Inc. of Oceanside, N.Y. The axial movement of the electrode 18 indicated at 36 is equal to the contact gap 28. When the active electrode surface 20 of the handpiece 12 held by the physician is pressed against the patient's skin, the electrode 18 is displaced from its first to a second position, compressing the spring 24, and with sufficient pressure the contact gap 28 is closed and the electrode shank 16 becomes electrically-connected to the fixed contact 30, and thus voltage available at the output connector 33 of the RF generator 34 becomes active on the active electrode surface 20 thus applying RF energy to the skin tissue. The first position of the electrode illustrated in FIG. 2 will be referred to as the RF-disconnected position, whereas the second position illustrated in FIG. 3 will be referred to as the RF-connected position. Note that placing the electrode 18 in contact with the skin does not energize the electrode with RF; the electrode must be displaced a certain distance, the contact gap 28, before the electrode becomes energized. Similarly, withdrawing the handpiece from the patient will first break the electrical contact internally as the spring expands and deenergizes the electrode before it breaks contact with the skin. While the internal contact end of the shank is shown as a cup, other shapes may be used if desired.

Figure 3:
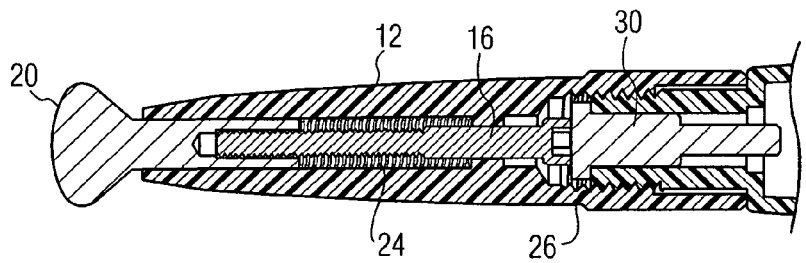
FIG. 3 is a cross-sectional view similar to FIG. 2 showing the electrode in its RF-connected position.
Figure 4:
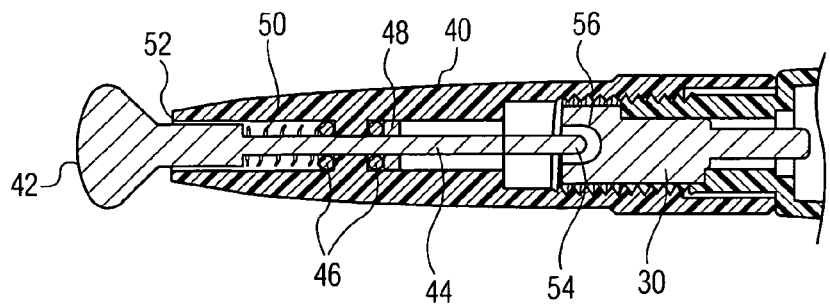
FIG. 4 is a cross-sectional view similar to FIG. 2 of a modified embodiment in accordance with the invention in the RF-disconnected position providing RF connection when the electrode is subjected either to axial or to lateral loading.

The embodiment illustrated in FIGS. 2 and 3 utilizes axial loading of the electrode to implement the RF-connecting position. FIG. 4 illustrates a modification wherein axial or lateral loading of the electrode applied by the physician is needed before energizing and deenergizing the electrode. In this embodiment, a handpiece 40 in accordance with the invention comprises an electrode 42 integral with a reduced diameter shank 44 supported by two elastic O-rings 46 for axial and lateral movement within the handle. A nut 48 fixed to the shank keeps the electrode from moving to the left under the biasing force of a spring 50 beyond the position shown in FIG. 4. The spaces 52 allow some lateral movement of the electrode, and the electrode can also move axially to the right until the shank end 54 contacts the surface of a cup-shaped end 56 of the fixed contact 30. The extension of the shank end 54 within the cup-shaped end 56 of the fixed contact allows both axial and lateral movement of the electrode 42 to effect the RF-connected position from the RF-disconnected position shown in the figure.

This result is possible because of the coaxial position of the shank end 54 within the cup-shaped end 56 of the fixed contact. A similar result can be obtained by mounting two concentric tubes spaced by rubber O-rings or similar elastomeric material such that the tubes do not touch when no load is applied to the electrode in front but will deflect and touch as in FIG. 4 when transverse or axial load is applied. In this case, one tube can be connected to the active cable from the generator and the second tube connected to the electrode.

Figure 5:
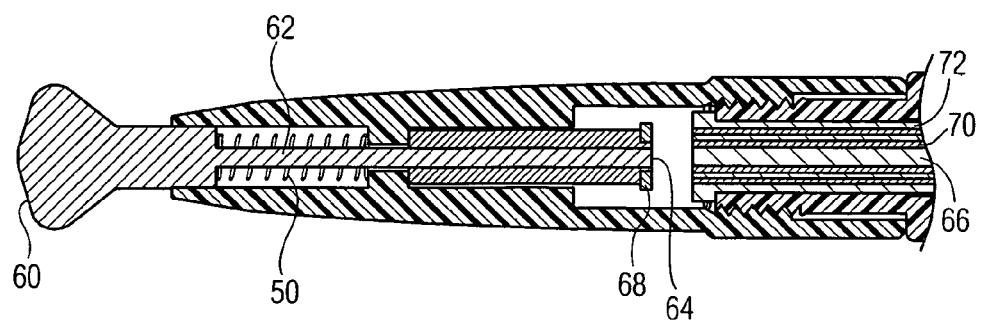
FIG. 5 is a cross-sectional view similar to FIG. 2 of a modified embodiment in accordance with the invention in the RF-disconnected position providing both RF connection and closing of a second circuit upon axial loading of the electrode.
Figure 6:
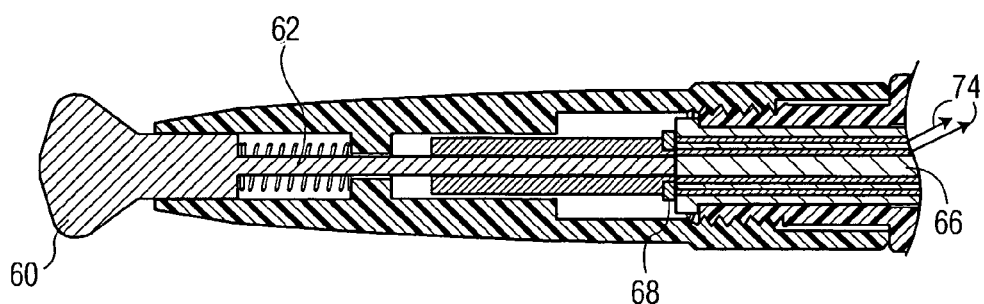
FIG. 6 is a cross-sectional view similar to FIG. 5 showing the handpiece in its RF-connected position.
Figure 8:
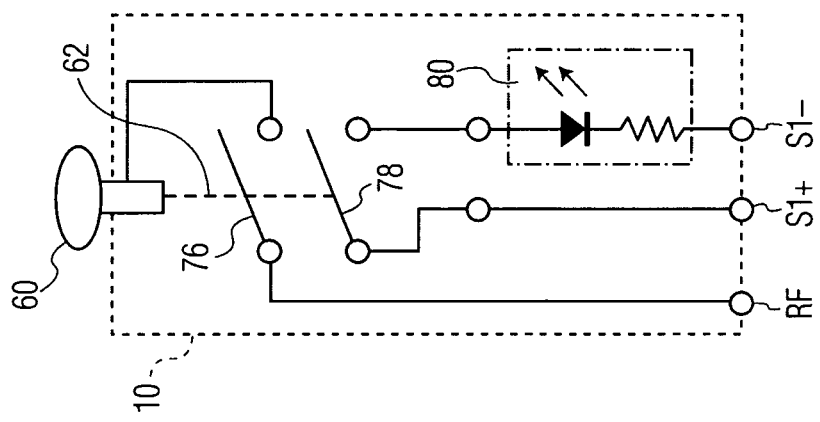
FIG. 8 is a circuit schematic similar to FIG. 7 showing how the second circuit can be used to activate an indicator light.
Figure 7:
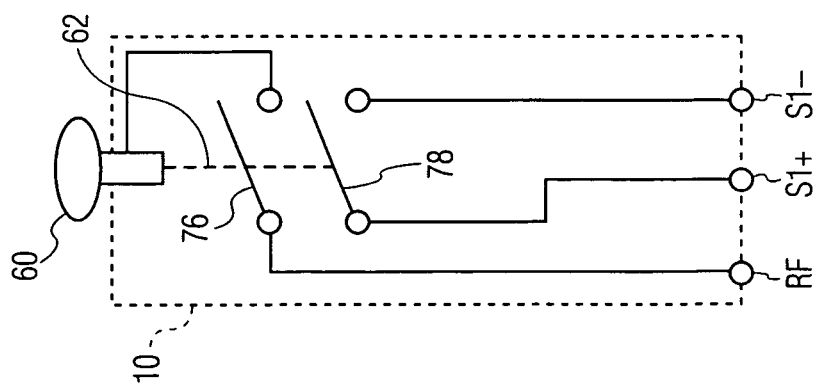
FIG. 7 is a circuit schematic schematically illustrating how loading of the electrode can connect the RF to the electrode as well as close the contacts of a second circuit.

FIGS. 5 and 6 show another embodiment in accordance with the invention with FIG. 5 showing the RF-disconnected position and FIG. 6 the RF-connected position similarly to the embodiment of FIGS. 2 and 3. In this case, when the electrode 60 is axially displaced as shown in FIG. 6, not only does the contact end 64 of the electrode shank 62 make RF connection with the fixed contact 66, but in addition, an electrically-conductive annular member 68, positioned on the internal shank end but electrically-insulated from the shank itself, contacts and shorts together two electrically-conductive cylinders 70, 72 mounted at the rear of the handpiece but electrically-insulated from the fixed contact 66. In other words, the movement of the electrode from its RF-disconnected position to its RF-connected position also closes a second circuit schematically illustrated at 74 that can be used for various purposes, as will be illustrated in FIGS. 7-9. This is essentially a double pole, single throw switch.

Figure 9:
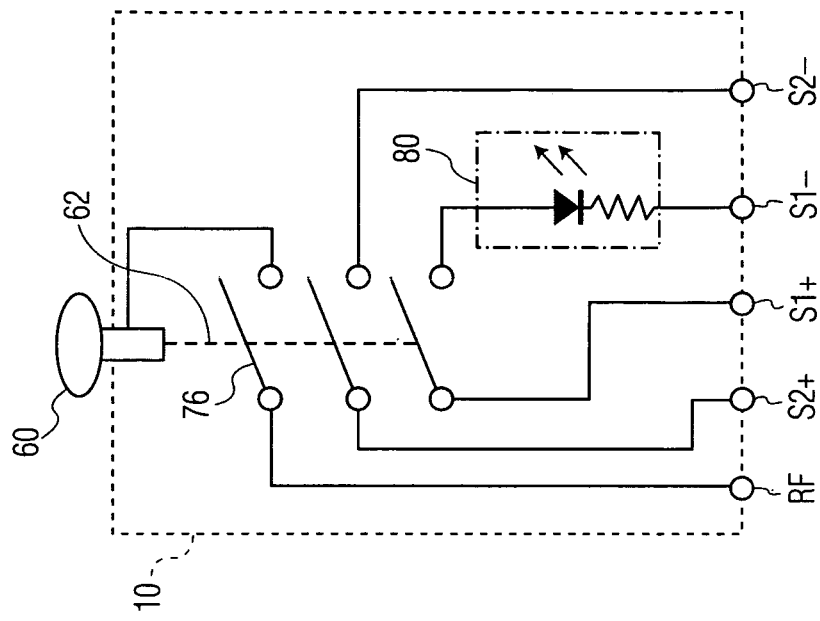
FIG. 9 is a circuit schematic similar to FIG. 7 based on the FIG. 5 embodiment showing how loading of the electrode can connect the RF to the electrode as well as close the contacts of both a second and a third circuit.

This double pole, single throw switch offers two sets of contacts (poles) that make or break through the same "push" action. The first 76 indicated in FIG. 7 at terminal RF is a direct connection from the electrode tip 60 to the RF energy source (central contact), while the second pole 78 allows current to flow between the cylinders 70, 72 to activate a control switch (not shown) on the generator which is connected to both lines (+/−) to control RF supply switching at the source. This second pole switch functions effectively like (and is wired in a similar manner identical to) the finger switch handpiece buttons and foot switch buttons—both legs of the switch are passed through the handpiece and onto the generator. This second switching circuit provided at terminals S1+ and S1− can also be used to activate a light 80 (FIG. 8), sound or tactile (vibration, click, etc.) signal to let the user know that the electrode 60 is active. This is typically accomplished through the existing generator circuitry, but could be incorporated within the handpiece itself as well Alternatively, multiple switches can be incorporated to be activated; for example, as shown in FIG. 9, a third switch provided at terminal S2+ and S2− can be incorporated for separate, isolated signaling, source activation and RF thru-circuits.

This entire spring-loaded electrode end scheme works to prevent shock to the patient essentially by moving the initial "spark" contact gap away from the patient's skin and puts the spark gap within the handpiece itself, and forces the user to make skin contact prior to RF energy being supplied. During release, the contact is opened first within the handle itself and not at the patient's skin.

The preceding embodiments relied on physical movement of the electrode immediately before energizing and immediately after deenergizing of the electrode by directly electrically connecting to or disconnecting from the energized cable. Indirect connection can also be effected, for example, magnetically or optically, by sensing movement or position of the electrode and using the generated signal to operate a relay effecting the required connection to the power source. Other common motion and position sensor types are well known by those skilled in the art and can be readily substituted to function in a similar manner. Using a signal this way is also described in the following embodiments.

In the following embodiment, the electrode is fixed to the handpiece and its contact with the patient's skin is sensed electrically before RF energy is supplied. In these embodiments, conventional handpieces can be used, for example, handpieces of the type illustrated in the two referenced incorporated pending applications. The electrical characteristic measured can be the capacitance impedance between the active electrode surface and the patient's skin. This can be measured internally of the RF generator or externally by a circuit of the type shown in FIG. 10. This circuit is somewhat similar to those used in charge transfer touch sensors used commercially in control panels, lighting controls, etc., in place of mechanical switches, except that this circuit maintains a relay closed while the sensor detects skin touch, and opens the relay when touch is removed.

Figure 10:
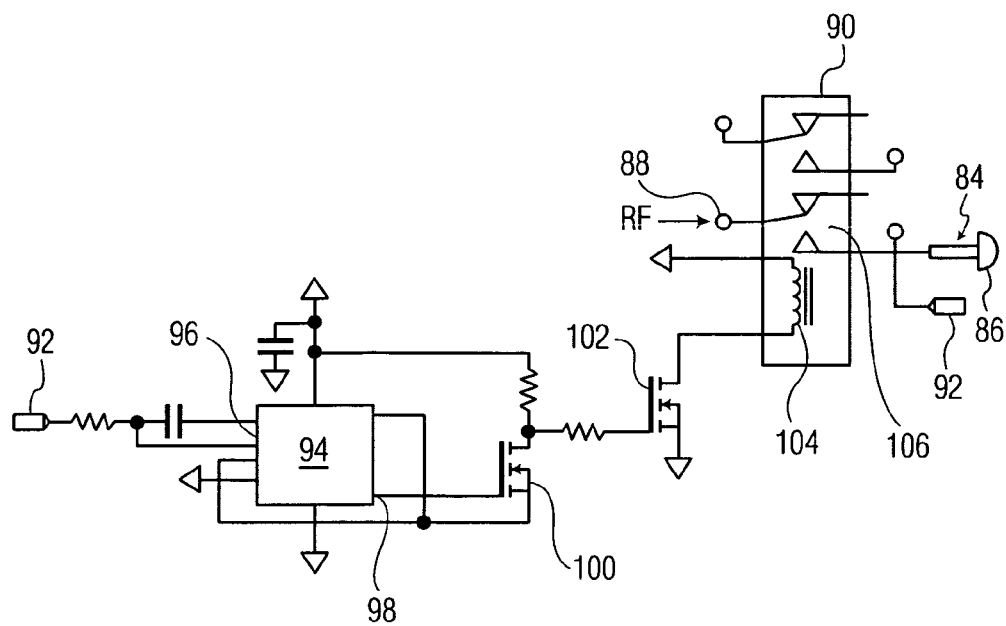
FIG. 10 is one form of a circuit schematic capable of responding to impedance changes at the electrode to sense skin contact and activate the RF generator.

The circuit of FIG. 10 is connected as shown to a typical conventional handpiece 84 having a dome electrode 86. RF power from the RF generator is supplied at terminal 88 of a relay 90 having 2 sets of contacts, the top set of which is unused for present purposes. A signal from the dome electrode 86 representing the capacitance of the electrode to the skin (recalling that the neutral electrode to the body is at ground potential) is derived at 92 and inputted at the left via a series-connected resistor and capacitor to a terminal 96 of a commercially available charge transfer touch sensor IC 94 which can be configured as is known by the choice of bias and other components to establish at an output terminal 98 a high value that turns on a signal transistor 100 which in turn drives a power transistor 102 that will via relay coil 104 operate the relay to switch the lower set of contacts 106 from the shown OFF position to the ON position, thus feeding RF power from the generator to the electrode 86. The active treatment electrode 86 may be coupled to the RF source through a known series capacitor (not shown), or some other mechanism to couple the RF portion of the RF signal to the treatment electrode 86 while isolating the DC portion of the RF signal from the treatment electrode to improve the touch-sensor circuit's sensing sensitivity, at the same time preventing the RF power from feeding back to the charge transfer circuit. So long as the sensed capacitance remains low during touch of the electrode to the skin, the relay 90 remains activated and the electrode is energized by the RF. As the electrode 86 starts to withdraw from the skin tissue, the capacitance rises quickly and the resultant signal switches the IC output 98 to a low value deactivating the relay and deenergizing the electrode. Other circuits can be readily devised by those skilled in this art to function similarly.

Figure 11:
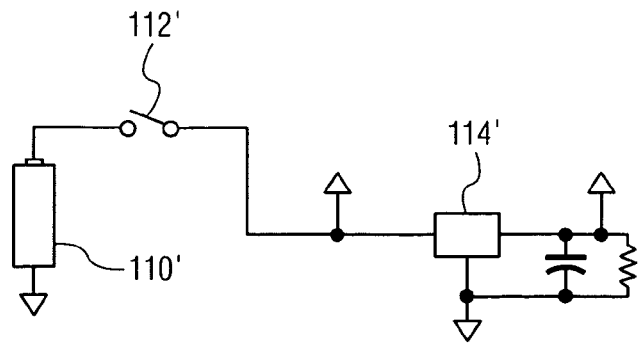
FIG. 11 is one form of a circuit schematic of a suitable power supply for the circuitry of FIG. 10.

The circuit of FIG. 10 can if desired be separately powered by a battery in a preferred embodiment as illustrated in FIG. 11, with the battery designated 110', and an on-off switch 112'. The battery may be connected to a conventional voltage regulator 114' to output constant operating voltages used by the sensing circuit. Any power source could be used for the sensing circuit but the circuit of FIG. 11 is a preferred embodiment that would allow it to be self contained and portable.

In a similar manner, the electrical characteristic measured could be the electrical impedance at the output connector at the generator, which is the impedance between the electrode surface and the usual neutral electrode in contact with the patient's body. In the absence of contact between the active electrode surface and the patient's skin, the impedance measured at the output connector will be of the order of Kohms.

As contact is made between the active electrode surface and the patient's skin, the measured impedance will drop to a value of the order of hundreds of ohms. That impedance change can be used to operate a relay as shown in FIG. 10 to pass the RF power to the electrode. Thus, the active electrode surface will become active when the output connector impedance drops, and when the electrode is withdrawn from the skin the output impedance rises deactivating the relay and deenergizing the output connector and thus the electrode.

Figure 12:
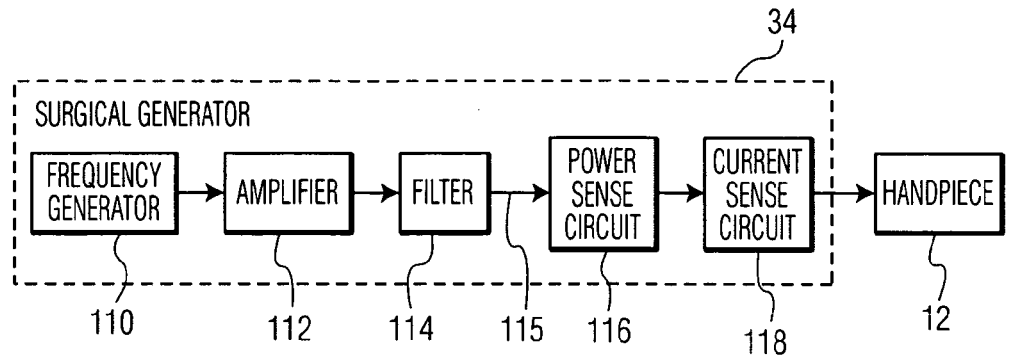
FIG. 12 is a block diagram of one form of RF generator incorporating means for sensing the output impedance of the RF generator.
Figure 13A:
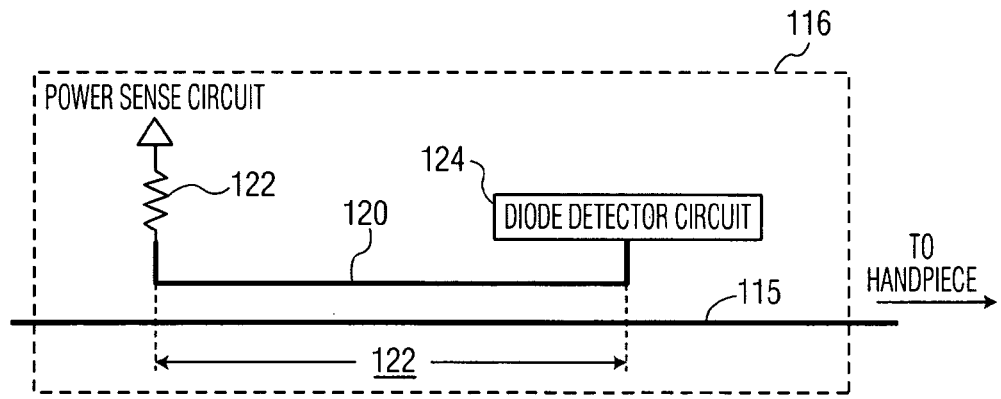
FIG. 13A is a schematic of one form of power sense circuit that can be employed in the generator of FIG. 12.
Figure 13B:
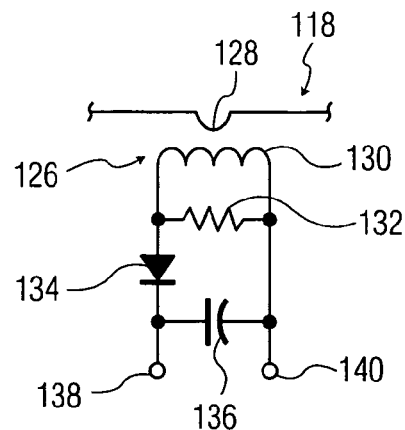
FIG. 13B is a schematic of one form of current sense circuit that can be employed in the generator of FIG. 12.

FIGS. 12, 13A and 13B illustrate one form of output impedance measuring circuit. FIG. 12 represents a basic block diagram of an RF generator, with a conventional frequency generator 110 whose output RF signal is fed into an amplifier 112 whose output in turn is fed through a filter 114. The resulting RF line 115 then passes through a power sensing circuit 116 and a current sensing circuit 118 before exiting the generator unit via a cable leading to the handpiece 12. FIG. 13A illustrates one possible embodiment of the power sensing circuit 116 utilizing a directional coupler, wherein the RF transmission line 115 is capacitively coupled to a conductive line 120 whose length 122 is equal to one quarter of the signal wavelength. The conductive line 120 is connected to a terminating resistor 122 and a diode detector circuit 124 which will measure the forward power on the RF transmission line 115.

FIG. 13B illustrates one possible embodiment of the current sensing circuit 118, where a line 128 having a primary winding in block 118 is carrying the current to be measured. The line is routed through a transformer 126 with the primary winding of the line 128 having fewer windings than the secondary winding 130 to step up the signal voltage across a resistor 132. The signal is then rectified by a diode 134 and smoothed by a capacitor 136 to create a DC voltage across terminals 138 and 140 that is proportional to the current on line 128.

Once the power and current have been determined as indicated in the forgoing circuits, then the impedance is readily determined by a calculation by known software or hardware dividing the power by the square of the current, which can then be used to activate a relay as described above.

FIGS. 1-13B illustrate a monopolar handpiece in accordance with the invention. Similar principles can be employed to implement the invention in a bipolar handpiece. In the monopolar handpiece, one pole of the RF power is not applied to the electrode until it contacts the tissue. In the application to a bipolar handpiece, both poles of the RF power are not applied to, respectively, both electrodes housed in the handpiece until contact with the tissue is made.

Figure 14:
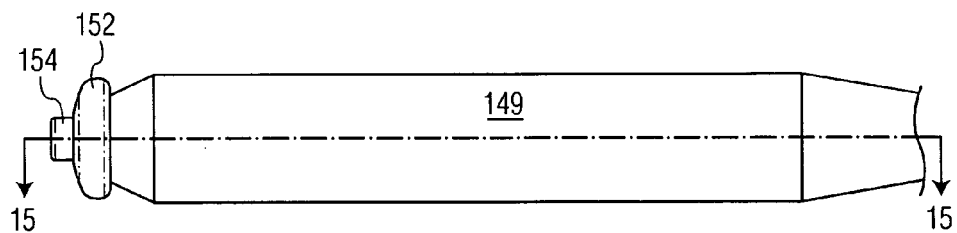
FIG. 14 is a side view of one form of a shock-free handpiece with a bipolar electrode according to the invention.
Figure 15:
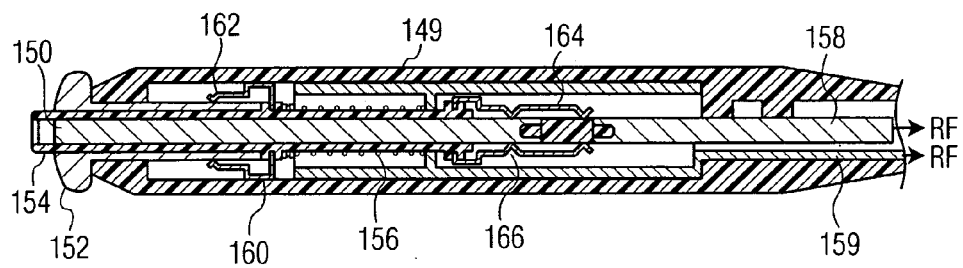
FIG. 15 is cross-sectional view along lines 15-15 of the handpiece of FIG. 14 showing the bipolar electrode in its RF-disconnected position.
Figure 16:
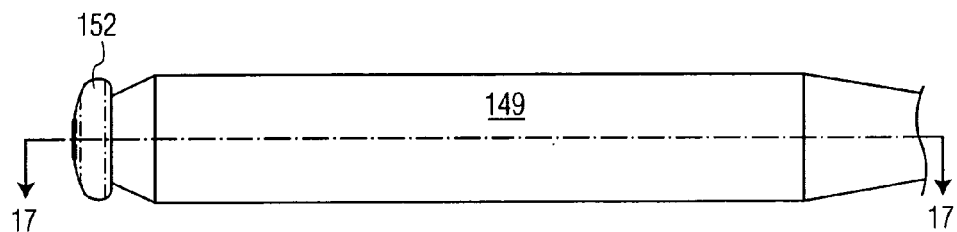
FIGS. 16 and 17 are views similar, respectively, to FIGS. 14 and 15 showing the bipolar electrode in its RF-connected position.
Figure 17:
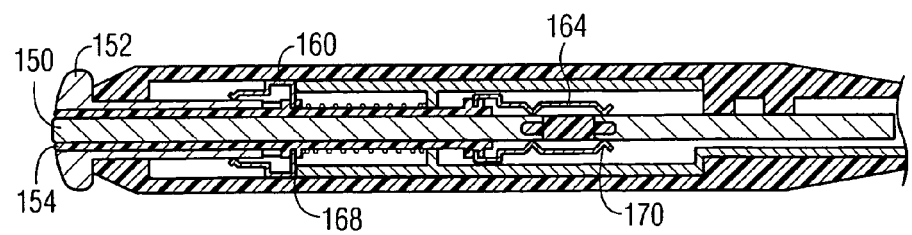

FIGS. 14 and 15 illustrate a bipolar handpiece having an insulating housing 149 with fixed inner 150 and outer 152 concentric electrodes with a spring-loaded, slidable, tubular insulator 154 surrounding the inner electrode 150, separating the two electrodes, and extending outward in front of the two electrodes. The spring is shown at 156 biasing the insulating tube into its RF-disconnected position. The RF power supplied from a cable (not shown) on the right is connected to electrical members 158 and 159. The tubular insulator 154 carries conductive spring loaded sliding connectors (or carriers), one of which 160 contacts the outer electrode 152 at 162, and the other of which 164 contacts the inner electrode 150 at 166. The extending insulator 154 acts as the arm of a double pole single throw switch, which is activated when the insulator tube is depressed as the physician brings the active end of the handpiece into contact with the patient's skin, simultaneously exposing the inner electrode (FIG. 17) and connecting both electrodes to their corresponding plus and minus RF sources (or poles) 158, 159. Note in FIG. 17 the carrier 160 at 168 in contact with conductive member corresponding to pole 159. The carrier 164 makes contact at 170 to the other pole 158. This embodiment uses these small contact springs 160, 164 attached to the insulator tube 154 which slide into contact with each pole 158, 159 of the effective switch to make and break contact as needed. The pre-contact inactive state is illustrated in FIG. 15, and the post-contact active state is illustrated in FIG. 17.

Figure 19:
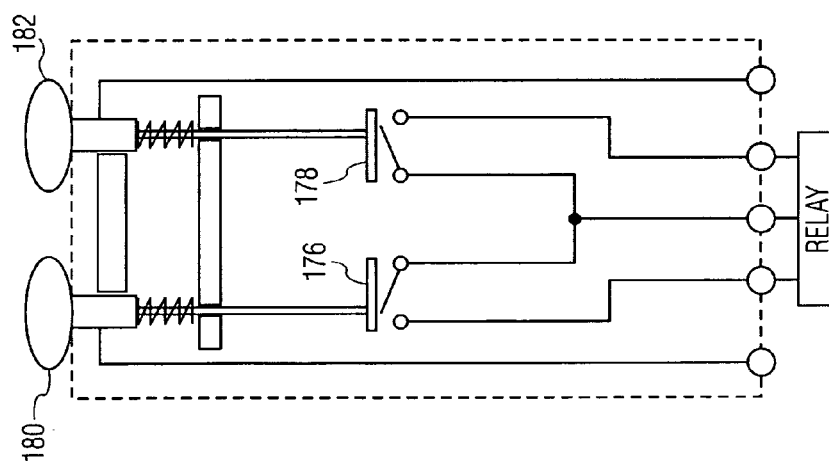
FIG. 19 is a circuit schematic schematically illustrating the operation of a first modified version of the bipolar embodiment of FIGS. 14-17.
Figure 18:
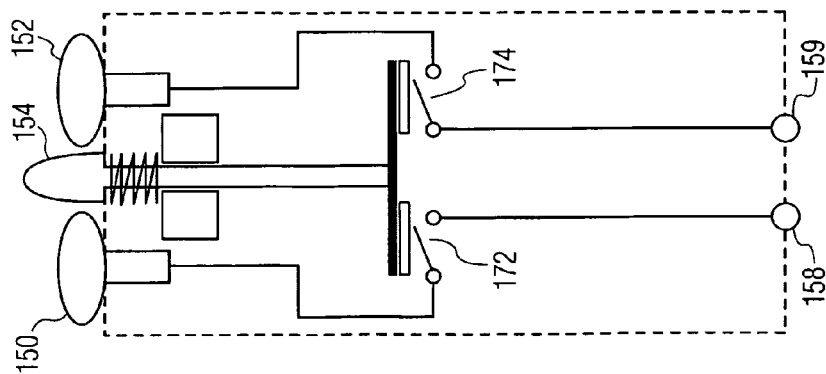
FIG. 18 is a circuit schematic schematically illustrating the operation of the bipolar embodiment of FIGS. 14-17.

The circuit schematic illustrating the operation is shown in simplified form in FIG. 18. Two separate normally off "momentary" switches 172, 174 make contact when the center post 154 is pushed in. FIG. 19 illustrates a modification that behaves effectively like two parallel versions of the monopolar embodiment, where the switches 176, 178 are activated by the depression of both spring-loaded bipolar electrodes 180, 182, activating a relay or relays which power the RF energy to each electrode. In this latter instance, it is preferred that the energy is supplied only when both switches 176, 178 have made contact, ensuring that both electrodes are in contact with the skin—this is readily implemented by a simple logic circuit that could be provided within the handpiece or within the switching circuitry of the energy source.

Figure 20:
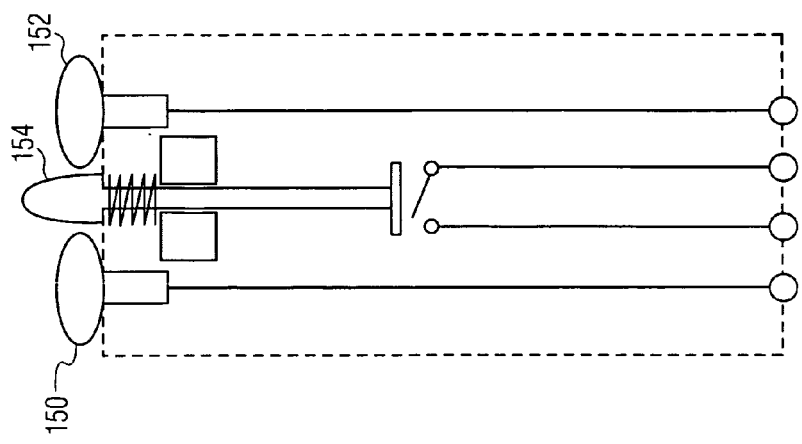
FIG. 20 is a circuit schematic schematically illustrating the operation of a second modified version of the bipolar embodiment of FIGS. 14-17.

FIG. 20 shows a third bipolar embodiment, a modified version of the FIG. 18 version with a movable central post 154 for accomplishing the switching to the fixed bipolar electrodes 150, 152. In this case, the central post 154 preferably switches a relay (not shown) on and off as needed to supply the RF power.

The FIG. 19 embodiment, effectively two parallel versions of the direct RF-switching monopolar embodiment working together, can also be implemented (not shown) like the FIG. 20 embodiment with the electrically "floating" electrodes 150, 152 switching directly with the RF supply rather than activating via relays.

The RF generator used preferably output RF currents in the range of about 0.2-10 MHz. Continuous wave power can be used.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A device for use in a surgical procedure for improving the appearance of skin tissue of a patient by applying RF energy thereto via a handpiece-supported electrode, the device comprising:
   (a) a handpiece having an electrical conductor configured to receive RF energy from a generator when activated, the handpiece supporting an electrode having an active surface to be brought into contact with the patient's skin to apply received RF energy to the skin when the generator is activated and while the electrode is pressed against the patient's skin, the handpiece comprising:
   (b) first switch means configured to electrically couple the electrode's active surface to the electrical conductor configured to receive RF energy when and while the active-surface urges against the patient's skin, wherein the first switch means comprises a first electrically conductive member coupled to the electrode and a second electrically conductive member electrically coupled to the electrical conductor configured to receive RF energy, wherein the first electrically conductive member is movable relative to a longitudinal axis of the handpiece in correspondence with the electrode surface between an RF-disconnected position and an RF-connected position, wherein the first electrically conductive member and the second electrically conductive member are configured to be electrically coupled with each other in the RF-connected position such that the electrode's active surface is electrically coupled to the electrical conductor configured to receive RF energy in the RF-connected position and electrically isolated from the electrical conductor configured to receive RF energy in the RF-disconnected position; and (c) a biasing member configured to urge the electrode toward the RF-disconnected position, wherein the biasing member is electrically isolated from the second electrically conductive member in the RF-disconnected position, wherein the electrode is movably supported by the handpiece, and the first electrically conductive member comprises an extension of the electrode positioned inside the handpiece, wherein the first electrically conductive member urges against the second electrically conductive member in the RF-connected position when the electrode urges against the patient's skin, and wherein the first electrically conductive member is spaced from the second electrically conductive member in the RF-disconnected position, wherein the electrode is laterally movable relative to the longitudinal axis between the RF-disconnected position and the RF-connected position, and the RF-disconnected and RF-connected positions define outermost extents of the electrode's movement.

2. A device as claimed in claim 1, wherein the electrode extension comprises a shank member extending parallel to the axis and connected to the electrode.

3. A device as claimed in claim 1, wherein the electrode is longitudinally movable relative to the longitudinal axis of the handpiece, and wherein the RF-disconnected and RF-connected positions define respective outermost extents of the electrode's movement.

4. A device as claimed in claim 1, wherein the electrode is longitudinally movable relative to the longitudinal axis between the RF-disconnected position and the RF-connected position, and the RF-disconnected and RF-connected positions define outermost extents of the electrode's movements.

5. A device as claimed in claim 1, wherein the first switch means defines a gap between the first electrically conductive member and the second electrically conductive member in the RF-disconnected position and wherein the first electrically conductive member and the second electrically conductive member urge against each other in the RF-connected position.

6. A device as claimed in claim 1, wherein the first electrically conductive member is urged toward the RF-disconnected position when the electrode's active surface is spaced from the patient's skin.

7. A device for use in a surgical procedure for improving the appearance of skin tissue of a patient by applying RF energy thereto via a handpiece-supported electrode, the device comprising:

(a) a handpiece having an electrical conductor configured to receive RF energy from a generator when activated, the handpiece supporting an electrode having an active surface to be brought into contact with the patient's skin to apply received RF energy to the skin when the generator is activated and while the electrode is pressed against the patient's skin, the handpiece comprising:

(b) first switch means configured to electrically couple the electrode's active surface to the electrical conductor configured to receive RF energy when and while the active-surface urges against the patient's skin, wherein the first switch means comprises a first electrically conductive member coupled to the electrode and a second electrically conductive member electrically coupled to the electrical conductor configured to receive RF energy, wherein the first electrically conductive member is movable relative to a longitudinal axis of the handpiece in correspondence with the electrode surface between an RF-disconnected position and an RF-connected position, wherein the first electrically conductive member and the second electrically conductive member are configured to be electrically coupled with each other in the RF-connected position such that the electrode's active surface is electrically coupled to the electrical conductor configured to receive RF energy in the RF-connected position and electrically isolated from the electrical conductor configured to receive RF energy in the RF-disconnected position; and (c) a biasing member configured to urge the electrode toward the RF-disconnected position, wherein the biasing member is electrically isolated from the second electrically conductive member in the RF-disconnected position, wherein the electrode is movably supported by the handpiece, and the first electrically conductive member comprises an extension of the electrode positioned inside the handpiece, wherein the first electrically conductive member urges against the second electrically conductive member in the RF-connected position when the electrode urges against the patient's skin, and wherein the first electrically conductive member is spaced from the second electrically conductive member in the RF-disconnected position, wherein the extension of the electrode comprises an electrically-conductive segment, and the handpiece further comprises second and third electrical conductors, wherein the second and third electrical conductors are so spaced from each other as to be electrically open, wherein the electrically-conductive segment is so positioned as to span a gap between the second and third electrical conductors and to electrically couple the second and third electrical conductors to each other when the electrode is in the RF-connected position.

8. A device as claimed in claim 7, wherein the handpiece further comprises second switch means configured to be activated when the first switch means is switched.

9. A device as claimed in claim 7, wherein the handpiece further comprises multiple switch means configured to be activated when the first switch means is switched.

10. A device for use in a surgical procedure for improving the appearance of skin tissue of a patient by applying RF energy thereto via a handpiece-supported electrode, the device comprising:

(a) a handpiece having an electrical conductor configured to receive RF energy from a generator when the generated is activated, the handpiece supporting an electrode having an active surface to be brought into contact with the patient's skin to apply received RF energy to the skin when the generator is activated and while the electrode is pressed against the patient's skin, the handpiece comprising:

(b) a first switch having a first electrically conductive member coupled to the electrode and a second electrically conductive member electrically coupled to the electrical conductor configured to receive RF energy, wherein the first electrically conductive member is movable relative to a longitudinal axis of the handpiece in correspondence with the electrode surface between an RF-disconnected position and an RF-connected position, wherein the first electrically conductive member and the second electrically conductive member are configured to be electrically coupled with each other in the RF-connected position such that the electrode's active surface is electrically coupled to the electrical conductor configured to receive RF energy in the RF-connected position and electrically isolated from the electrical conductor configured to receive RF energy in the RF-disconnected position; and (c) a biasing member configured to urge the electrode toward the RF-disconnected position, wherein the first electrically conductive member comprises an extension of the electrode positioned inside the handpiece to urge against the second electrically conductive member in the RF-connected position when the electrode urges against the patient's skin, and wherein the first electrically conductive member is spaced from the second electrically conductive member in the RF-disconnected position, wherein the extension of the electrode comprises an electrically-conductive segment, and the handpiece further comprises second and third electrical conductors, wherein the second and third electrical conductors are so spaced from each other as to be electrically open, wherein the electrically-conductive segment is so positioned as to span a gap between the second and third electrical conductors and to electrically couple the second and third electrical conductors to each other when the electrode is in the RF-connected position.

11. A device for use in a surgical procedure for improving the appearance of skin tissue of a patient by applying RF energy thereto via a handpiece-supported electrode, the device comprising:

(a) a handpiece having an electrical conductor configured to receive RF energy from a generator when the generated is activated and an electrode defining an active surface configured to contact a patient's skin for applying RF energy to the skin, the handpiece comprising:

(b) an electrically conductive extension from the electrode, the extension being positioned within the handpiece;

(c) a second electrically conductive member electrically coupled to the electrical conductor configured to receive RF energy, wherein the extension is movable relative to a longitudinal axis of the handpiece in correspondence with the electrode surface between an RF-disconnected position and an RF-connected position, wherein the extension and the second electrically conductive member electrically couple with each other in the RF-connected position by urging together in the RF-connected position and electrically isolated from each other in the RF-disconnected position by being spaced apart from each other in the RF-disconnected position; and (c) a biasing member configured to urge the electrode and the corresponding extension toward the RF-disconnected position;

(d) a first auxiliary electrical conductor laterally spaced from the electrical conductor configured to receive RF energy and a second auxiliary electrical conductor laterally spaced from the first auxiliary electrical conductor and the electrical conductor configured to receive RF energy, wherein the extension from the electrode comprises an electrically conductive segment sized to span a gap between the first auxiliary electrical conductor and the second auxiliary electrical conductor and positioned to electrically couple the first auxiliary electrical conductor and the second auxiliary electrical conductor to each other with the electrode is positioned in the RF-connected position.

* * * * *